(12) United States Patent
Bhattacharya

(10) Patent No.: US 12,209,892 B1
(45) Date of Patent: Jan. 28, 2025

(54) METHOD AND APPARATUS FOR BREATH-HOLD MONITORING IN DIAGNOSTIC AND THERAPEUTIC PROCEDURES

(71) Applicant: EmpNia Inc., Edina, MN (US)

(72) Inventor: Manojeet Bhattacharya, Edina, MN (US)

(73) Assignee: EmpNia Inc., Edina, MN (US)

( * ) Notice: Subject to any disclaimer, the term of this patent is extended or adjusted under 35 U.S.C. 154(b) by 0 days.

(21) Appl. No.: 18/900,208

(22) Filed: Sep. 27, 2024

Related U.S. Application Data

(63) Continuation-in-part of application No. 18/409,081, filed on Jan. 10, 2024, which is a continuation of application No. 17/224,855, filed on Apr. 7, 2021, now Pat. No. 12,044,556, which is a continuation-in-part of application No.
(Continued)

(51) Int. Cl.
| | |
|---|---|
| G01D 5/353 | (2006.01) |
| A41D 13/12 | (2006.01) |
| A61B 5/00 | (2006.01) |
| G01L 1/24 | (2006.01) |
| G02B 6/02 | (2006.01) |

(52) U.S. Cl.
CPC ..... *G01D 5/35316* (2013.01); *A41D 13/1281* (2013.01); *A61B 5/6804* (2013.01); *G01D 5/35335* (2013.01); *G01D 5/35367* (2013.01); *G01L 1/246* (2013.01); *G02B 6/022* (2013.01)

(58) Field of Classification Search
None
See application file for complete search history.

(56) References Cited

U.S. PATENT DOCUMENTS

| | | | |
|---|---|---|---|
| 4,868,381 A | 9/1989 | Davis | |
| 4,909,260 A | 3/1990 | Salem et al. | |
| (Continued) | | | |

FOREIGN PATENT DOCUMENTS

| | | |
|---|---|---|
| CN | 111317481 A | 6/2020 |
| JP | H0775627 A | 3/1995 |
| (Continued) | | |

OTHER PUBLICATIONS

Anzai Medical, Co., Ltd, "Respiratory Gating System AZ-733V1: What is a Respiratory Gating System," http://www.anzai-med.co.jp, No. date given, 4 pages.
(Continued)

*Primary Examiner* — Jerry Rahll
(74) *Attorney, Agent, or Firm* — COOLEY LLP

(57) ABSTRACT

A method for compensating for dynamic changes in a body of a patient during a controlled interaction with the body includes acquiring data from at least one sensing device disposed on the body and detecting a change along at least one optical fiber of the sensing device caused by dynamic changes associated with the body during the controlled interaction. A respiratory gating signal is generated based on the change along the at least one optical fiber of the sensing device measured over time. The method further comprises controlling relative movement between the body and an interactive device in response to the respiratory gating signal to compensate for the dynamic changes associated with the body during the controlled interaction.

30 Claims, 10 Drawing Sheets

Related U.S. Application Data

PCT/US2020/065691, filed on Dec. 17, 2020, which is a continuation-in-part of application No. 16/723,352, filed on Dec. 20, 2019, now Pat. No. 11,041,740.

(56) References Cited

U.S. PATENT DOCUMENTS

| | | | |
|---|---|---|---|
| 5,545,993 | A | 8/1996 | Taguchi et al. |
| 5,907,403 | A | 5/1999 | Andrews et al. |
| 6,475,153 | B1 | 11/2002 | Khair et al. |
| 7,077,810 | B2 | 7/2006 | Lange et al. |
| 7,257,436 | B2 | 8/2007 | Sasaki et al. |
| 7,678,063 | B2 | 3/2010 | Felmlee et al. |
| 8,553,959 | B2 | 10/2013 | Hsieh et al. |
| 8,655,441 | B2 | 2/2014 | Fletcher et al. |
| 9,088,130 | B2 | 7/2015 | Kim et al. |
| 9,116,055 | B2 * | 8/2015 | Johnston ............ G01K 11/3206 |
| 9,304,018 | B2 * | 4/2016 | Davis ................... A61B 5/1079 |
| 9,730,654 | B2 | 8/2017 | Erbel et al. |
| 9,841,331 | B2 * | 12/2017 | Wood .................. A61B 5/1036 |
| 9,987,503 | B2 * | 6/2018 | Grass ....................... A61B 6/12 |
| 10,234,934 | B2 * | 3/2019 | Connor ................. G06F 3/017 |
| 10,321,873 | B2 * | 6/2019 | Connor ................ A61B 5/6831 |
| 10,332,644 | B2 | 6/2019 | Garcia |
| 10,488,916 | B2 * | 11/2019 | Hahami ............... A61B 5/6805 |
| 10,524,701 | B2 * | 1/2020 | Kim .................... A61B 5/6847 |
| 10,716,510 | B2 * | 7/2020 | Connor ................ A61B 5/6804 |
| 11,041,740 | B1 | 6/2021 | Bhattacharya |
| 11,504,010 | B2 | 11/2022 | Bhattacharya |
| 2008/0045813 | A1 | 2/2008 | Phuah et al. |
| 2008/0146947 | A1 | 6/2008 | Kojima et al. |
| 2009/0185772 | A1 | 7/2009 | Xia et al. |
| 2009/0234240 | A1 | 9/2009 | Kuenzler et al. |
| 2013/0035587 | A1 | 2/2013 | Lagendijk et al. |
| 2013/0211261 | A1 | 8/2013 | Wang et al. |
| 2014/0064332 | A1 * | 3/2014 | Johnston ............ G01K 11/3206 374/161 |
| 2014/0088377 | A1 * | 3/2014 | Manzke ............... A61B 5/1073 600/595 |
| 2014/0128721 | A1 * | 5/2014 | Forthmann .......... A61B 5/1128 600/407 |
| 2014/0238153 | A1 * | 8/2014 | Wood ................... A43B 23/029 73/862.627 |
| 2014/0268099 | A1 | 9/2014 | Moslehi |
| 2015/0124266 | A1 * | 5/2015 | Davis ................... A61B 5/1079 356/601 |
| 2015/0359455 | A1 * | 12/2015 | Hahami ............... A61B 5/6804 600/476 |
| 2015/0359467 | A1 | 12/2015 | Tran |
| 2016/0202755 | A1 * | 7/2016 | Connor ................... G06F 3/011 73/865.4 |
| 2016/0256710 | A1 | 9/2016 | Goldstein et al. |
| 2016/0338644 | A1 * | 11/2016 | Connor ................ A61B 5/1126 |
| 2016/0361194 | A1 * | 12/2016 | Hautvast ................ A61B 18/24 |
| 2017/0007849 | A1 * | 1/2017 | Hautvast ............... A61N 5/1001 |
| 2017/0049341 | A1 | 2/2017 | Karabacak et al. |
| 2017/0354353 | A1 * | 12/2017 | Kim ........................ G01L 1/246 |
| 2018/0008196 | A1 * | 1/2018 | Connor ................ A61B 5/1126 |
| 2018/0364115 | A1 * | 12/2018 | Brown ....................... B32B 7/12 |
| 2019/0298265 | A1 | 10/2019 | Keating et al. |
| 2019/0336038 | A1 * | 11/2019 | Gorgutsa ............. A61B 5/0816 |
| 2021/0186340 | A1 | 6/2021 | Bhattacharya |
| 2021/0190549 | A1 | 6/2021 | Bhattacharya |
| 2021/0223068 | A1 | 7/2021 | Bhattacharya |
| 2023/0070912 | A1 | 3/2023 | Bhattacharya |
| 2024/0032816 | A1 | 2/2024 | Bhattacharya |
| 2024/0210218 | A1 | 6/2024 | Bhattacharya |

FOREIGN PATENT DOCUMENTS

| | | |
|---|---|---|
| JP | 2014525764 A | 10/2014 |
| JP | 2015231512 A | 12/2015 |
| JP | 2017506543 A | 3/2017 |
| JP | 2017506555 A | 3/2017 |
| JP | 2017519221 A | 7/2017 |
| WO | WO-2012168836 A2 | 12/2012 |
| WO | WO-2013180085 A1 | 12/2013 |
| WO | WO-2015128179 A1 | 9/2015 |
| WO | WO-2015128392 A1 | 9/2015 |
| WO | WO-2015167340 A1 | 11/2015 |
| WO | WO-2016147795 A1 | 9/2016 |
| WO | WO-2017037479 A1 | 3/2017 |
| WO | WO-2017190085 A1 | 11/2017 |
| WO | WO-2019031041 A1 | 2/2019 |
| WO | WO-2021127207 A1 | 6/2021 |
| WO | WO-2021127233 A1 | 6/2021 |
| WO | WO-2022020519 A1 | 1/2022 |
| ZA | 200508066 B | 1/2007 |

OTHER PUBLICATIONS

Davies, Justine et al., "Beyond Blood Pressure: Pulse Wave Analysis—a Better Way of Assessing Cardiovascular Risk?" Future Cardiology, pp. 69-78, (2005).

De Jonckheere, J., et al.; "Ofseth: A breathing motions monitoring system for patients under MRI," 32nd Annual International Conference of the IEEE EMBS, 2010, 1016-1019.

Esper, Stephen A. et al., "Arterial Waveform Analysis," Best Practice & Research Clinical Anaesthesiology 28 pp. 363-380, (2014).

International Search Report and Written Opinion for International Application No. PCT/US2020/065691, mailed Jun. 1, 2021, 25 pages.

Invitation to Pay Additional Fees for PCT Application No. PCT/US2020/065691, dated Apr. 9, 2021, 20 pages.

Katsuragawa Yui, et al., "Non-invasive Blood Pressure Measurement by Pulse Wave Analysis Using FBG Sensor," 2015 IEEE International Instrumentation and Measurement Technology Conference (I2MTC) Proceedings, IEEE, May 11, 2015, pp. 511-515.

Khan, Yasser et al., "A Flexible Organic Reflectance Oximeter Array", Proceedings of the National Academy of Sciences 115 (47), pages E11015-E11024; Washington, DC, Nov. 2018.

Lau, Doreen, et al. "Intensity-Modulated Microbend Fiber Optic Sensor for Respiratory Monitoring and Gating During MRI," IEEE Transactions on Biomedical Engineering, vol. 60, No. 9, Sep. 2013, pp. 2655-2662.

Lee, Hooseok et al., "Reflectance Pulse Oximetry: Practical Issues and Limitation," The Korean Institute of Communications and Information Services, ScienceDirect, 195-198 Nov. 2016.

Lui, J. et al., "Evaluation of the combined use of two different respiratory monitoring systems for 4D CtTsimulation and gated treatment," Journal of Applied Clinical Medical Physics, Wiley 19:5 pp. 666-675, (2018).

Niekic, Paula "Pulse Contour Cardiac Output (PiCCO) Learning Package," Liverpool Hospital Intensive Care Unit, Feb. 29, 2016, 17 pages.

Office Action for Japanese Application No. 2023-130280, mailed Sep. 17, 2024, with English translation, 9 pages.

Office Action for Japanese Application No. JP20220538314 with English translation, dated May 1, 2023, 8 pages.

Office Action for Japanese Application No. JP20220538314 with English translation, dated Nov. 7, 2023, 10 pages.

Office Action for U.S. Appl. No. 16/723,352, dated Nov. 24, 2020, 9 pages.

Roylance, David, "Stress-Strain Curves, Department of Materials Science and Engineering," Massachusetts Institute of Technology, Cambridge, MA, Aug. 23, 2001, 14 pages.

* cited by examiner

METHOD AND APPARATUS FOR BREATH-HOLD MONITORING IN DIAGNOSTIC AND THERAPEUTIC PROCEDURES

CROSS-REFERENCE TO RELATED APPLICATIONS

This application is a continuation-in-part of U.S. patent application Ser. No. 18/409,081, filed Jan. 10, 2024, entitled "Method and Apparatus for Real Time Respiratory Gating Signal Generation and Detection of Body Deformation Using Embedded Fiber Bragg Gratings," which is a continuation of U.S. patent application Ser. No. 17/224,855, filed Apr. 7, 2021, entitled "Method and Apparatus for Real Time Respiratory Gating Signal Generation and Detection of Body Deformation Using Embedded Fiber Bragg Gratings," (now U.S. Pat. No. 12,044,556), which is a continuation-in-part of International Patent Application No. PCT/US2020/065691, filed Dec. 17, 2020, entitled "Method and Apparatus for Real Time Respiratory Gating Signal Generation and Detection of Body Deformation Using Embedded Fiber Bragg Gratings," which designates the U.S. and is published in English, and which is a continuation-in-part of U.S. patent application Ser. No. 16/723,352 (now U.S. Pat. No. 11,041,740), filed Dec. 20, 2019, entitled "Method and Apparatus for Real Time Respiratory Gating Signal Generation and Detection of Body Deformation Using Embedded Fiber Bragg Gratings," the disclosure of each of which is incorporated herein by reference in its entirety.

BACKGROUND

Anatomic and functional imaging modalities such as computed tomography (CT), magnetic resonance imaging (MRI), and positron and single photon emission tomography (PET and SPECT) suffer from image degradation due to respiratory motion of the patient. And even though in some instances of CT scans the patient is asked to hold their breath during the image acquisition, this is not always feasible as not all patients can hold their breath due to their age and/or physical condition. Additionally, breath hold CT scans are typically higher radiation dose scans as the scan needs to be completed quickly which can only be accomplished by increasing the X-ray flux and moving the table quickly. In external beam (photon and particle) radio-therapy the intensity and/or the range is modulated and the beam is raster scanned over the tumor or other disease tissue for delivering the maximum dose to the tumors or other disease tissues while minimizing the dose delivered to the surrounding healthy tissue, which is the concept of conformal therapy. Since internal organs, as well as tumors and disease tissues, move with the human body due to respiratory motion, the effectiveness of intensity or range modulated external beam therapy is critically dependent on respiratory motion compensation. Similar to external beam radiotherapy, compensation for respiratory motion is also desirable for emerging applications of directed energy-based image-guided therapeutic procedures (e.g., focused ultrasound therapies, radiofrequency (RF) therapies, laser therapies, etc.).

Currently, there are three main types of respiratory motion management devices in use. One, the "Anzai" method, uses a wearable belt with electrical strain sensors that is affixed near the diaphragm of the patient. Shortcomings of this method include the fact that motion is being measured at one plane only, and the device cannot be in the field of view either during an imaging scan or therapy procedure as it distorts the image and the treatment field due to its high attenuating property.

The second class of method uses optical techniques (such as Varian RPM, C-Rad and GateCT) using either physical markers or reflectors on the patient from where a light signal is reflected and a motion signal is derived, or a structured light is mapped onto the patient. The shortcomings of this method include the fact that the light reflections can be modified significantly by objects in the path including patient clothing or covers that can lead to significant discomfort to the patient, as the patient must remain bare bodied during the procedure in a room that is typically kept colder for managing equipment heating. These methods are harder to implement in imaging than in therapy because most imaging procedures are performed in the bore of the device that does not provide a clear direct line of sight to the patient. In some other cases, a thermal scanner is used to track the breathing motion of the patient and suffers from the same shortcomings as the optically scanning techniques.

The third type uses X-ray sources and detection systems for generating a moving X-ray image of the patient for managing motion during therapy. The shortcomings of this method include the need for significant infrastructure for installation, the requirement of a direct line of sight, and unnecessary added radiation dose to the patient for motion management. In addition, the sensitivity of MRI systems for electromagnetic interference is a problem for implementing motion management techniques. As such, there are no currently available effective motion management techniques for this diagnostic imaging modality.

SUMMARY

In some embodiments, a method for compensating for dynamic changes in a body of a patient during a controlled interaction with the body includes acquiring data from at least one sensing device disposed on the body and detecting a change along at least one optical fiber of the sensing device caused by dynamic changes associated with the body during the controlled interaction. A respiratory gating signal is generated based on the change along the at least one optical fiber of the sensing device measured over time. The method further comprises controlling relative movement between the body and an interactive device in response to the respiratory gating signal to compensate for the dynamic changes associated with the body during the controlled interaction. In some embodiments, the at least one sensing device includes at least one fiber Bragg grating (FBG). In such embodiments, the data acquired from the at least one sensing device is wavelength data from the at least one FBG, the change along the at least one optical fiber is effective shifts of Bragg wavelengths in the wavelength data, and the respiratory gating signal is based on the effective shifts of the Bragg wavelengths.

In some embodiments, a method of compensating for dynamic changes in a body of a patient during a controlled interaction with the body includes acquiring wavelength data from at least one fiber Bragg grating (FBG) disposed on the body and detecting effective shifts of Bragg wavelengths in the wavelength data. The effective shifts are caused by dynamic changes associated with the body during the controlled interaction. A respiratory gating signal is generated based on the effective shifts of the Bragg wavelengths measured over time. The method further includes controlling an interactive device, based on the respiratory gating signal, to pause the controlled interaction during the dynamic changes associated with the body.

In some embodiments, a method of compensating for dynamic changes in a body of a patient during a controlled interaction with the body includes acquiring wavelength data from at least one fiber Bragg grating (FBG) disposed on the body and detecting effective shifts of Bragg wavelengths in the wavelength data. The effective shifts are caused by dynamic changes associated with the body during the controlled interaction. A respiratory gating signal is generated based on the effective shifts of the Bragg wavelengths measured over time. The method further includes controlling a scanning device based on the respiratory gating signal such that image data is not acquired during the dynamic changes associated with the body.

In some embodiments, a method of compensating for dynamic changes in a body of a patient during a controlled interaction with the body includes acquiring wavelength data from at least one fiber Bragg grating (FBG) disposed on the body and detecting effective shifts of Bragg wavelengths in the wavelength data. The effective shifts are caused by dynamic changes associated with the body during the controlled interaction. A respiratory gating signal is generated based on the effective shifts of the Bragg wavelengths measured over time. The method further includes (i) controlling a scanning device, based at least in part on the respiratory gating signal, to acquire image data of a target region of the body while compensating for the dynamic changes associated with the body, and (ii) controlling an interactive device, based at least in part on the respiratory gating signal and the acquired image data, to perform the controlled interaction with the target region.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

Figure 1A:
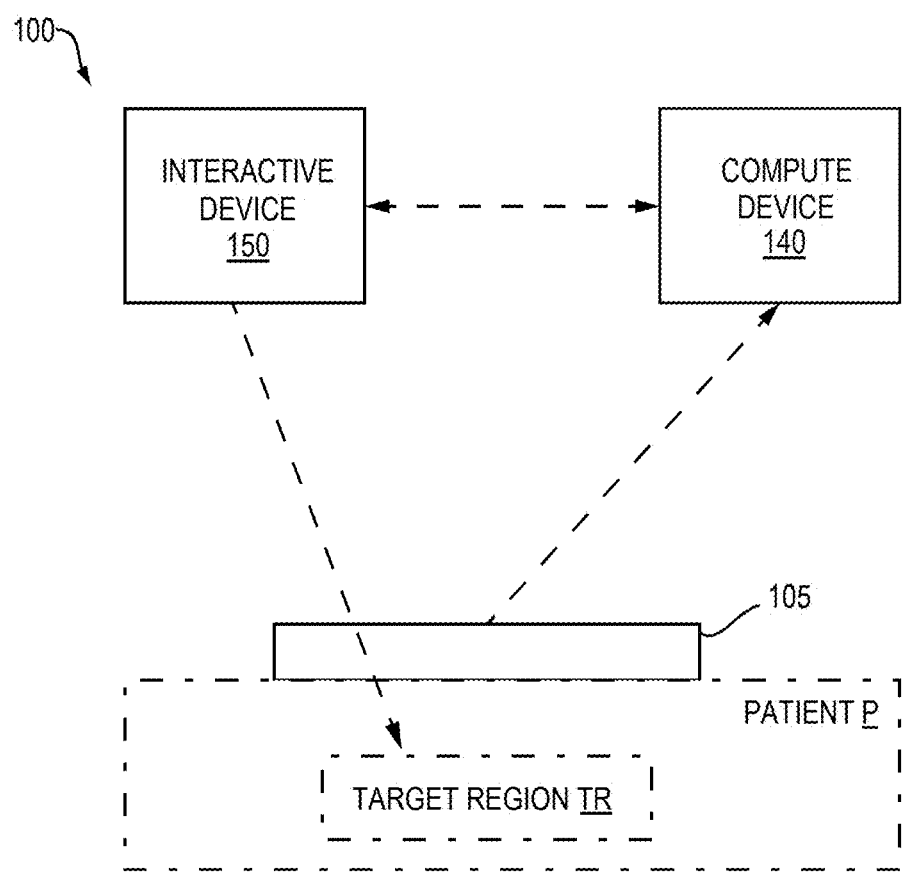
FIG. 1A is a representative system for compensating for dynamic changes in a body of a patient during a controlled interaction with the body, according to an embodiment.

Embodiments consistent with the principles of the present invention include methods and systems of compensating for dynamic changes associated with a body of a patient (e.g., body deformation, respiratory motion, and/or the like) during a controlled interaction (e.g., image acquisition, therapeutic interactions, image-guided interactions or interventions, and/or the like). In one embodiment, as image data of a body is acquired, the system acquires peak wavelength data from a plurality of fiber Bragg gratings (FBGs) disposed on the body, with the FBGs aligned along a cartesian coordinate system on the body. Through the FBGs, the system detects effective shifts of the Bragg wavelengths of the FBGs caused by body deformation during image acquisition. The system corrects the acquired image data during image reconstruction to compensate for body deformation and/or respiratory motion during an image scan based on the effective shifts of the Bragg wavelengths of the FBGs aligned along the cartesian coordinate system.

In some embodiments, the system may be used in connection with data acquired through a computed tomography (CT) scan, a magnetic resonance imaging (MRI) scan, a positron emission tomography (PET) scan, a single photon emission computed tomography (SPECT) scan, or a Fluoroscopy scan.

In other embodiments, the system may include moving a body relative to a scanning device (e.g., through a cavity of the scanning device) and acquiring volumetric image data of a body on a slice by slice basis. The system acquires peak wavelength data from a plurality of fiber Bragg gratings (FBGs) disposed on the body. The system detects effective shifts of the Bragg wavelengths of the FBGs caused by body deformation during image acquisition and controls the movement of the body through the cavity of the scanning device, such that the body does not move and image data is not acquired during body deformation or certain phases of the respiratory cycle based on the effective shifts of the Bragg wavelengths of the FBGs.

Another embodiment consistent with principles of the invention includes a system for compensating for dynamic changes associated with a body of a patient (e.g., body deformation, respiratory motion, and/or of the like) during external beam treatment, such as photon beam radiotherapy or proton beam therapy used in connection with the treatment of tumors. In one embodiment, a target region of the body for external beam treatment is identified. The system acquires peak wavelength data from a plurality of fiber Bragg gratings (FBGs) disposed on a body, the FBGs aligned along a cartesian coordinate system. The system directs external beam treatment to the target region. As effective shifts of the Bragg wavelengths of the FBGs caused by dynamic changes associated with a body of a patient (e.g., body deformation, respiratory motion, and/or of the like) during treatment are detected, the external beam treatment may be redirected to compensate for the dynamic changes during an image scan based on the effective shifts of the Bragg wavelengths of the FBGs aligned along the cartesian coordinate system to maintain focus on the target region.

Another embodiment consistent with principles of the invention includes a wearable such as a garment for real time detection of body deformation during an image scan includes a front portion, made of a compression material and having of plurality of fiber Bragg gratings (FBGs), the front portion disposed on top of a person body, the FBGs aligned along a cartesian coordinate system. The garment includes a plurality of light emitters, each light emitter configured to pulse light waves through a corresponding FBGs and a plurality of light sensors, each light sensor attached to a corresponding FBG and configured to receive pulsed light waves. A processor obtains data through a data acquisition module configured to receive from the light sensors peak wavelengths reflected by the FBG. The processor, which may be embedded in the garment or located remote device or terminal, also includes a comparator configured to determine the effective shifts of Bragg wavelengths due to axial strain on the FBGs. In yet another embodiment, a garment for real time detection of body deformation during an image scan may have FBGs disposed all around a body.

The processor may further include a correction module configured to correct acquired image data to compensate for body deformation during an image scan based on the effective shifts of the Bragg wavelengths of the FBGs aligned along the cartesian coordinate system, or to re-direct an external beam treatment to compensate for body deformation during an image scan based on the effective shifts of the Bragg wavelengths of the FBGs aligned along the cartesian coordinate system to maintain focus on the target region.

A description of example embodiments shown in the drawings follows.

FIG. 1A is a system 100 for compensating for dynamic changes in a body of a patient P during a controlled interaction with the body, according to an embodiment. The system 100 includes a sensing device 105, a compute device 140, and an interactive device 150. The sensing device 105 is configured to be placed and/or in contact with the body of the patient P in a position corresponding to a target region TR. The target region TR can correspond to tissue or a portion of the body for which it is desirable to perform a controlled interaction. As used herein, a controlled interaction can refer to image acquisition, therapeutic or treatment interactions (e.g., external beam treatment), image-guided interactions or interventions (e.g., image-guided interventional surgery), and/or the like.

The sensing device 105 can be any suitable sensing device. For example, the sensing device 105 can be an optical fiber-based sensing device configured to detect dynamic changes associated with the body of the patient P based on, for example, changes along one or more optical fibers. For example, in some embodiments, the sensing device 105 can be an optical fiber having any number of fiber Bragg gratings (FBGs), as described in further detail herein. The sensing device 105 can be configured to provide relatively high-frequency and/or high-sampling rate data collection allowing for substantially real-time compensation of dynamic changes associated with the body of the patient P (and/or at least dynamic changes associated with the target region TR) during a controlled interaction.

The compute device 140 included in the system 100 is configured to receive signals from the sensing device 105 and to perform one or more operations, processes, functions, etc. configured to determine and/or calculate a dynamic change associated with the target region TR based on data received from the sensing device 105. For example, the sensing device 105 can detect movement due to respiration or other functions of the body. Based on signals received from the sensing device 105, the compute device 140 can determine, for example, a current or changed position of the target region TR and/or a magnitude, direction, velocity, acceleration, etc. associated a change in the target region TR.

The interactive device 150 included in the system 100 is configured to receive and/or send signals from/to the compute device 140. In some embodiments, the compute device 140 and the interactive device 150 can be embodied, disposed, and/or otherwise a part of a single or the same machine. In other embodiments, the compute device 140 can be remote from the interactive device 150 and communication can be established via one or more wired or wireless networks (not shown in FIG. 1A).

The interactive device 150 can be any suitable device configured to interact with the body of the patient P. For example, the interactive device 150 can be an imaging device such as a computed tomography (CT) device, a magnetic resonance imaging (MRI) device, and positron emission tomography (PET) device, a single photon emission computed tomography (SPECT), and/or the like. In some embodiments, the interactive device 150 can be an external beam treatment device (e.g., a focused energy treatment device, a radiation beam treatment or external beam radiotherapy device, a photon beam therapy device, a proton beam therapy device, and/or the like). In some embodiments, the interactive device 150 can be a combination of devices such as an image-guided external beam therapy device, image-guided interventional device (e.g., used in biopsy procedures, guided placement of interventional devices, etc.), and/or the like.

In some implementations, the interactive device 150 can be used in and/or can be used to perform a controlled interaction (e.g., image and/or treat) with the target region TR of the body. During the controlled interaction, the body of the patient P and/or at least the target region TR of the patient P may move due to voluntary or involuntary movement, respiratory motion, cardiac or other organ motion, tumor motion, body deformation, and/or the like. The sensing device 105 can be positioned on the body and used to detect dynamic changes and/or movement of the body of the patient P. The compute device 140 can be configured to determine, calculate, define, and/or otherwise characterize the dynamic changes associated with at least the target region TR. In addition, the compute device 140 can be configured to determine how such dynamic changes would change and/or alter the controlled interaction being performed by the interactive device 150. Accordingly, the compute device 140 can be configured to at least partially control the interactive device 150 (and/or send signals that are operable in controlling the interactive device 150) so that the interactive device 150 compensates, adjusts, and/or accounts for the dynamic changes of the body (or at least of the target region TR) during the controlled interaction, as described in further detail herein.

Figure 1B:
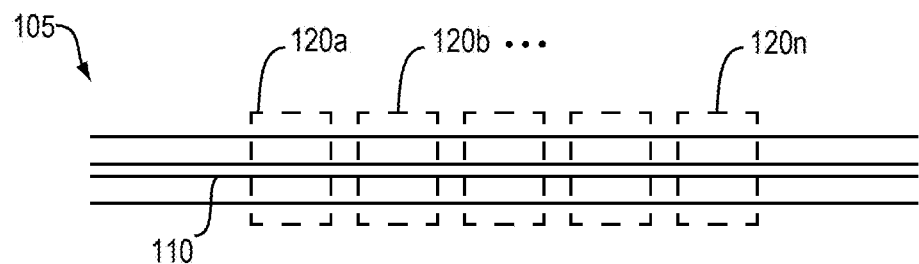
FIG. 1B is a representative fiber-core including multiple sensors.

FIG. 1B is a representative schematic drawing of the sensing device 105 shown in FIG. 1A. As described above, the sensing device 105 can be, for example, an optical fiber-based sensing device. As shown, the sensing device 105 includes at least an optical fiber 110 (also referred to a fiber-core) and a number of sensors 120a-n. The sensing device 105 can be used in any suitable system(s) and method(s) of compensating for dynamic changes associated with a body of a patient (e.g., body deformation, respiratory motion, and/or the like) during a controlled interaction (e.g., image acquisition, therapeutic interactions, image-guided interactions or interventions, and/or the like). For example, the sensing device 105 can be placed on a desired portion of the body of the patient such that movement, deformation, and/or changes associated with the body result in one or more changes along the optical fiber 110, which in turn, are detected by the sensors 120a-n. In some embodiments, such a sensing device 105 can include a single optical fiber including the sensors 120a-n or multiple optical fibers (each of which include a number of sensors 120a-n) arranged in any suitable manner. The optical fiber 110 can be at least temporarily coupled to the body of the patient (e.g., via an adhesive strip or the like), embedded in any suitable wearable, garment, etc., and/or the like.

The sensor(s) 120a-n of the sensing device 105 are included in and/or positioned along the optical fiber 110. The sensor(s) 120a-n can be any suitable optical-based or light-based sensor. In some implementations, the use of fiber optic-based sensor(s) (e.g., the sensor(s) 120a-n) can allow for high-frequency and/or high-sampling rate data collection associated with changes along the optical fiber 110. The high-frequency and/or high-sampling rate data collection can be desirable for substantially real-time compensation of dynamic changes associated with a body of a patient during a controlled interaction. The sensor(s) 120a-n can be, for example, functional or non-functional fiber optic sensors, light transmission fiber optic sensors, FBGs, and/or the like. While embodiments herein are described as including FBGs, it should be understood that the embodiments are provided by way of example only and not limitation. Similar systems, embodiments, and/or methods are possible using other fiber optic-based sensor(s) and such systems, embodiments, and/or methods can be functionally similar to or substantially the same as (e.g., functionally equivalent to) the systems, embodiments, and/or methods described herein.

Figure 1C:
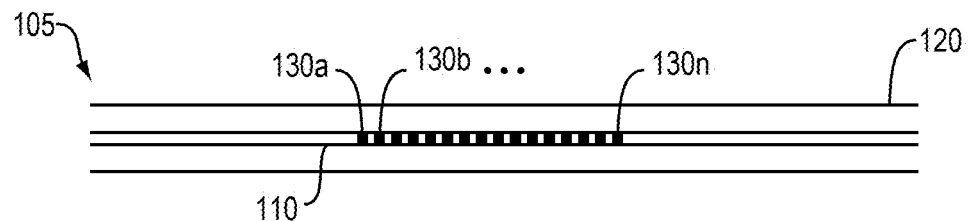
FIG. 1C is a representative FBG in a fiber-core.

As illustrated in FIG. 1C, a fiber Bragg grating (FBG) 120 is a small length of optical fiber 110 that comprises a plurality of reflection points 130a-n that create a periodic variation of refractive index. The FBG reflects a unique wavelength ($\lambda B$), centered around a bandwidth, $\Delta\lambda B$. The periodicity $\Lambda$ of the grating is related to the Bragg wavelength $\lambda B$:

$$\lambda B = 2n_{eff}\Lambda \quad (1)$$

$n_{eff}$ is the effective refractive index of the single-mode photosensitive fiber. As the fiber is stretched and the grating parameter $\Lambda$ increases by $\delta\Lambda\Lambda$ while the effective refractive index $n_{eff}$ decreases by $\delta n_{eff}$, the Bragg wavelength $\lambda B$ shifts by:

$$\delta\lambda B = 2\{n_{eff}\delta\Lambda + \Lambda\delta n_{eff}\} \quad (1a)$$

By embedding one or more optical fibers with one or more FBG in wearable materials that can be wrapped over parts of anatomically relevant parts of the human body can be used to sense the deformation of that part resulting from physiological processes such as breathing. In certain embodiments consistent with principles of the invention, the deformation data may be used to correct certain distortions caused by the deformation during image acquisition. In other embodiments, the deformation data may be used to assist in the targeted deliverance of certain medical treatments by altering the delivery to compensate for motion induced by respiration. In other embodiments, the time variations of the strain sensing and the distortion may be used to derive a gating signal for physiological processes. Similarly stated, the effective shifts in the Bragg wavelengths can be used to determine and/or derive a gating signal associated physiological processes (e.g., body deformation, respiratory motion, tumor motion, organ motion, and/or any other dynamic changes associated with the body).

Before one can use the embedded FBG as a strain gauge, the FBG's response function and linearity should be characterized as a function of load. To characterize the FBG's response function and linearity, an electrical strain gauge may be used to calibrate the FBG such that the applied tensile loading approximates readings of the displacement of the body within the Cartesian coordinate system for a three-dimensional object. For the FBG to perform as a reliable strain gauge, the change in the reflection wavelength of the FBG as it gets stretched under tensile load must linearly track the electrical strain gauge data. Once calibrated, the response of an FBG may be reliably used as an embedded strain gauge for detecting object surface deformation.

Within reasonable limits on the elasticity of the gauge, it may also be used for detecting the degree to which the object surface has been displaced. Based on a calibration curve comparing pressure against strain or wavelength, along with the strain data from the sensors, one can detect the degree of displacement. In other cases, the calibration curves may be derived from comparing reflected Bragg wavelengths to secondary respiratory measurements that can include physical or image-based measurements. In yet other cases, absolute and/or global calibrations may not be necessary and the relative changes in reflected wavelengths may be sufficient for the measurements of respiratory motion.

Figure 2B:
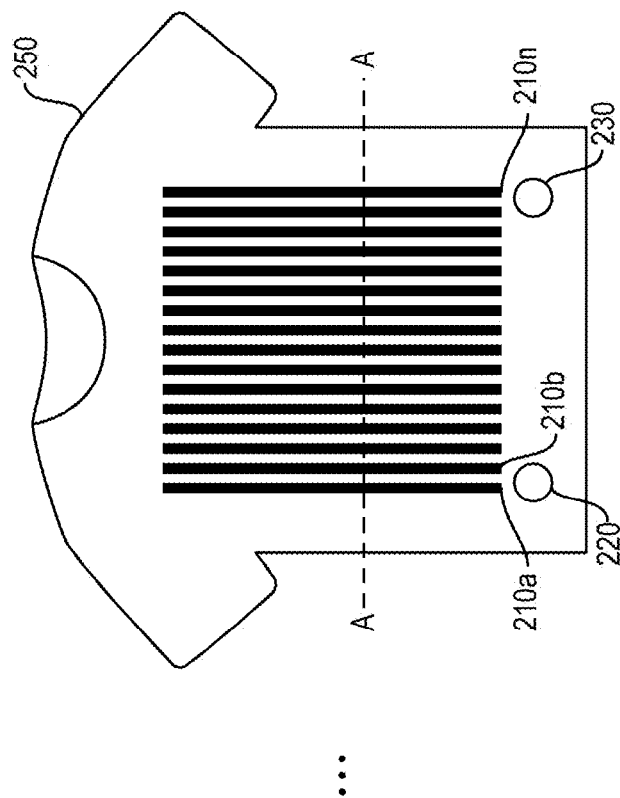
FIGS. 2A and 2B are embodiments of a garment that may be used during an image scan for real time detection of body deformation according to principles of the present invention.
Figure 2A:
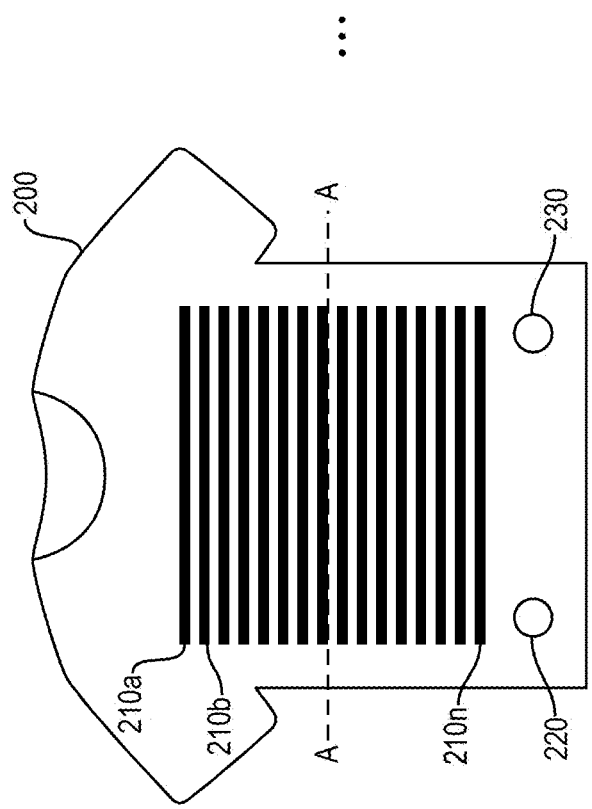

FIGS. 2A and 2B are embodiments of a garment 200 and 250 that may be used during an image scan for real time detection of dynamic changes and/or body deformation according to principles of the present invention. In the garment 200 shown in FIG. 2A, a plurality of FBG fibers 210a-n is embedded laterally along the garment, running in a direction parallel to a scanning plane A. In the garment 250 shown in FIG. 2B, a plurality of FBG fibers 210a-n is embedded longitudinally along the garment, running in a direction perpendicular to a scanning plane A. In both embodiments, the garments 200 and 250 may have an input 220 for a laser or light source that is transmitted through the FBG fibers 210a-n. Each FBG 210a-n in connected to a light sensor (not shown) that receives pulsed light waves from the light sources. In addition, the garments 200 and 250 may also include an output 230, where the light sensors may provide data concerning the light transmission through each of the FBGs 210a-n to an external processor that can identify shifts in the effective Bragg wavelengths of the FBGs 210a-n, suggesting changes and/or deformations in the surface of the object within the garment. In other embodiments, the processor may be internal to the garments 200 and 250, and transmit data via a wireless transmission, such as WiFi or Bluetooth. The multiple FBGs 210a-n can help identify where in the cross-sectional scanning plane there may be specific movement, as each provides a different longitudinal marker along a cartesian coordinate system. Given the low attenuation properties of the garments 200 and 250 and that the fiber optic sensors do not create electromagnetic interference, these embodiments may be used both while imaging as well as during therapy.

In addition, the change in wavelength measured over time for a free breathing patient wearing such a garment (or donning any of the devices described herein) represents the patient specific respiratory signal. The respiratory signal can be used as a gating signal for imaging and/or therapy (or any other controlled interaction(s)) in a similar fashion as is used today from respiratory gating devices such as the Anzai belt, the RPM device, the C-Rad system, and the VisionRT system. The added benefit in this case is that the gating device can be in the imaging and/or therapy field of view without inducing imaging artifacts and/or therapy interference. In some embodiments, the respiratory gating signal may help monitor a voluntary breath hold, such as a Respiratory Deep Inspiration Breath Hold or Expiration Breath Hold. In general, a voluntary breath hold is a practice used when dealing with controlled interactions with a patient (e.g., imaging, therapeutic interactions, interventional procedures (with or without image guidance), and/or the like). For example, when using a voluntary breath hold, the particular interaction (whether image scanning or therapeutic interaction) is delivered only at certain points during the patient's breathing cycle of deep inspiration or expiration. The patient may be asked to take a deep breath in (or deep breath out) and hold their breath for some period. This breath hold limits body deformation and/or excursion, and tumor/organ motion for the duration of the hold, allowing for more controlled interactions. Some embodiments can generate and/or can be configured to generate a respiratory gating signal and/or the like that can indicate that the patient has engaged in the voluntary breath hold (either inspirational or expirational), released the hold, and/or that there has been a voluntary or involuntary excursion associated with, for example, starting or ending the breath hold. Moreover, embodiments herein can control the interaction(s) with the body of the patient based at least in part on the respiratory gating signal. Therapeutic interactions may include an external beam treatment, directed energy-based treatments (e.g., focused energy, ultrasonic energy, laser energy, RF energy, etc.), or they may include interventional procedures such as needle biopsy and/or catheter placement. The interventional procedures can include image guided interventional procedures and/or image guided placement of an interventional device.

Figure 3:
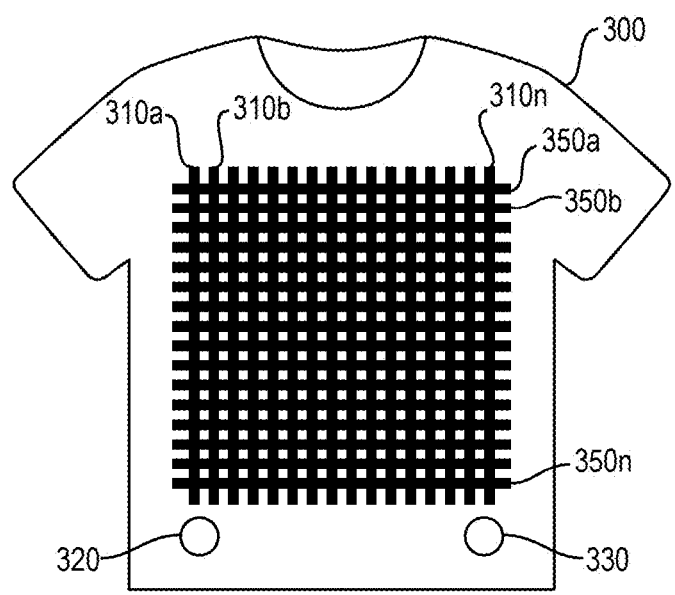
FIG. 3 is second embodiment of a garment that may be used during an image scan for real time detection of body deformation according to principles of the present invention.

FIG. 3 is another embodiment of a garment 300 that may be used during an image scan for real time detection of dynamic changes and/or body deformation according to principles of the present invention. In this garment, a plurality of FBG fibers 310a-n is embedded longitudinally along the garment 300, and another plurality of FBG fibers 350a-n is embedded latitudinally along the garment 300. In addition, the garment 300 may also include an output 330, where the light sensors may provide data concerning the light transmission through each of the FBGs 310a-n and FBGs 350a-n to an external processor that can identify shifts in the effective Bragg wavelength of the FBGs 310a-n and FBGs 350a-n, suggesting changes and/or deformations in the surface of the object within the garment 300. In other embodiments, the processor may be internal to the garment 300, and transmit data via a wireless transmission, such as WiFi or Bluetooth. Similar to FBGs 210a-n of the garments 200 and 250, the multiple FBGs 310a-n can help identify where in the cross-sectional scanning plane there may be specific movement, as each provides a different longitudinal marker along a cartesian coordinate system. The addition of FBGs 350a-n provides additional data responsive to movements within the object within the garment 300 in a different plane, allowing for more precise information concerning the location and intensity of the movement.

In embodiments of the garment with embedded FBGs for real time measurement of the deformation (e.g., dynamic changes) of the patient body under respiration, one may embed a number of FBGs using a predetermined coordinate system, such as a cartesian coordinate system or polar coordinate system. Additionally, the predetermined coordinate system may be determined in such a way as to balance competing interests of maximizing the fidelity of the measured deformation map while also using the least number of embedded FBGs. This could mean that the embedded FBGs are aligned along a coordinate system with respect to the patient's body or in other cases they could be located for a pseudorandom sampling of the patient's body. In some embodiments, this could mean that the FBGs could be distributed such that a concentration of embedded FBGs is aligned in a relatively dense distribution in one region, and loosely distributed in others. Depending on the nature of the garment, the distribution of FBGs within the garment may vary, as a belt or shirt may have a different, more contoured fit around a body than a blanket. Additionally, multiple FBGs can be inscribed inside a single mode optical fiber, and as long as they are separated by a predetermined and/or desired distance from each other and that each of these FBGs have a unique and distinct Bragg wavelength, a single such optical fiber can be used to measure the strain along its length using a single broadband light source and a single wavelength multiplex detection system. Such a system has distinct advantages over an electrical strain gauge-based system as in the latter case each strain gauge needs its own electrical connection.

By embedding one or more optical fibers with one or more FBGs in wearable materials that can be wrapped or otherwise placed over parts of anatomically relevant parts of the human body, the one or more FBGs can be used to sense the motion resulting from physiological processes such as breathing, heart beats, and blood flow, or those resulting from movement of the patient. In certain embodiments consistent with principles of the invention, the motion data may be used to correct certain distortions caused by the motion during image acquisition. In other embodiments, the motion data may be used to assist in the targeted deliverance of certain medical treatments by altering the delivery to compensate for motion induced by respiration, heart beats, blood flow, or patient movements.

In another embodiment, detection of such motion can be used for physiological monitoring of the patient particularly in the case where the patient is under sedation, or the patient is a pediatric patient. The detected motion signals can be used to interrupt the imaging or the therapy procedure for patient safety or other clinical reasons.

Figure 4:
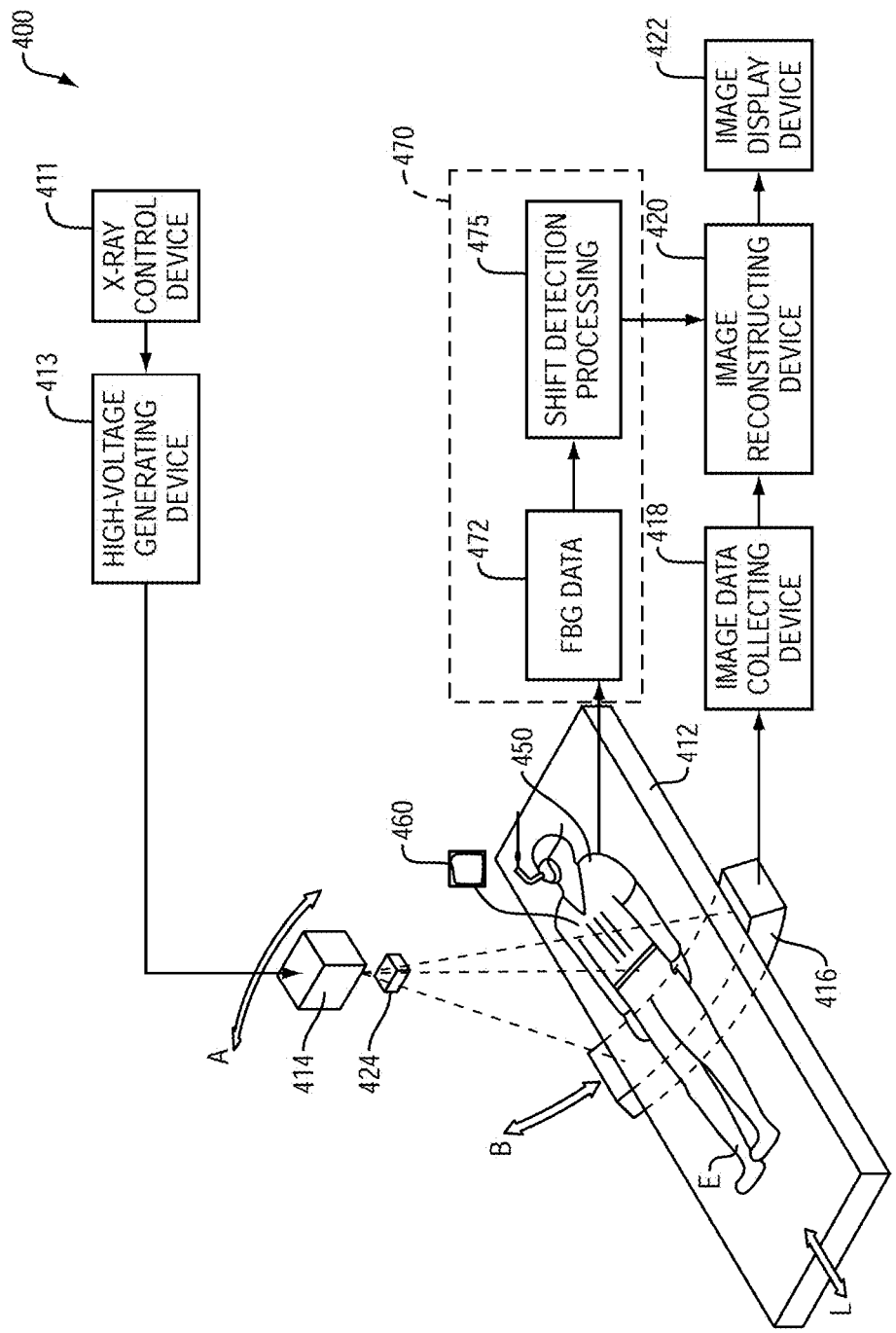
FIG. 4 is an exemplary medical imaging system in which embodiments consistent with the present invention may be used.

FIG. 4 is a medical imaging system 400 in which embodiments consistent with the present invention may be used. The medical imaging system 400 may be a computed tomography (CT) scanner including an X-ray control device 411, a high-voltage generating device 413 for generating a high voltage according to a shot signal supplied from the X-ray control device 411, a table 412 displaceable in the direction indicated by the arrow L with an examinee E placed thereon, an X-ray source 414 for applying X-rays (photons) to the examinee E according to a high voltage supplied from the high-voltage generating device 413, an X-ray detector 416 for detecting photons that have passed through the examinee E, a data collection device 418 for collecting examinee-transmitted data based on photons detected by the X-ray detector 416, an image reconstruction device 420 for reconstructing a tomographic image of the examinee E from examinee-transmitted data collected by the data collection device 418. The X-ray source 414 and the X-ray detector 416 are rotatable in the directions indicated by the arrow A. The components described above make up a CT (Computed Tomography) apparatus. As the X-ray source 414 and the X-ray detector 416 rotate around the examinee E, the image data provides a cross-sectional image scan or "slice." As the examinee moves through the system along the direction L, multiple image "slices" are taken, providing a volumetric scan of the examinee. The system may further include an image display device 422 for displaying a reconstructed tomographic image on a CRT (Cathode Ray tube) or the like (or any other suitable display device).

In typical systems, the CT scanner must not rotate too slowly, and the table 412 must also not pass through too slowly, or respiratory motion or other dynamic changes during the scan will manifest in the body (e.g. abdominal or chest cavity) scans resulting in image artifacts in the reconstructed CT volume. With an increase in rotational speed of the CT scanner and translational speed of the table 412, the intensity of the X-ray source 414 must be higher to acquire adequate data for sufficient image resolution. However, the collision of photons with atoms and molecules of living tissue may cause damage to the tissue. The more photons that arrive per second from the X-ray source 414, measured as flux, the greater the potential for tissue damage.

Some embodiments consistent with principles of the present invention include a device (e.g., a wearable clothing like device or any other suitable device) with embedded FBGs for real time detection of respiratory motion and/or other dynamic changes in or of the body. In some embodiments consistent with principles of the invention, that device may be used as a respiratory gating device to concurrently control movement of the CT scanner and dosage of X-rays by separating the acquired data in various stages of the respiratory cycle and the state of the body habitus at that stage, thereby alleviating the need for and/or reliance on breath hold or averaging over respiratory cycle. As the device detects respiratory motion, the CT scanner may pause operation, and may resume when the body has returned to its initial respiratory state. Thus, the X-ray dose to the patient may be lowered if the patient can be co-scanned with a respiratory gating device. Similar applications are possible while using this device in a PET scan, SPECT scan, Fluoroscopy scan, etc. to enable low dose imaging by reducing the injected radiopharmaceutical dose while maintaining diagnostic image quality because of reduced artifacts due to respiratory motion and/or other dynamic changes.

In other embodiments, the device (e.g., a wearable clothing device or any other suitable device) may be operated to continuously detect respiratory motion and the degree of deformation resulting from respiratory displacement, such that image data may be acquired without interruption or pausing, with the deformation data used in image reconstruction for deformation correction.

Figure 10:
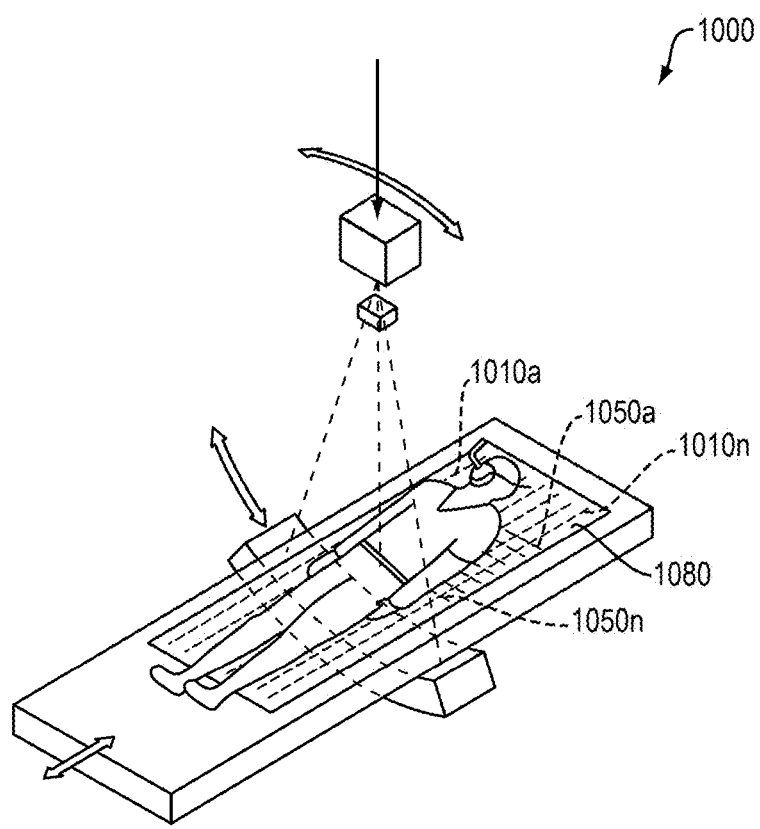
FIG. 10 is an exemplary patient handling system including an embodiment consistent with principles of the invention.

In yet other embodiments, as illustrated in FIG. 10, a patient handling system 1000 may include padding 1080 that has fibers containing the FBGs embedded similar to the garments illustrated in FIGS. 2A, 2B and 3. As shown in FIG. 10, a plurality of FBG fibers 1010a-n is embedded longitudinally along the padding 1080, and another plurality of FBG fibers 1050a-n is embedded latitudinally along the padding. In alternate embodiments consistent with the teachings herein, the padding 1080 may have FBGs embedded in other configurations to provide data relating to movement, deformation, or displacement of a body on the padding. Such fibers can also be embedded directly in the patient handling systems (patient beds) of medical imaging and radiation therapy devices. As with the garments shown in FIGS. 2A, 2B and 3, the padding may include an output (not shown), where light sensors may provide data to an external processor.

The FBGs may be used to obtain both the deflection of the bed under a patient specific loading as well as a respiratory signal and/or the like from the patient in contact with the bed. Both of these parameters may be used for optimizing the image acquisition of the patient and for the therapy delivery to the patient.

Figure 5A:
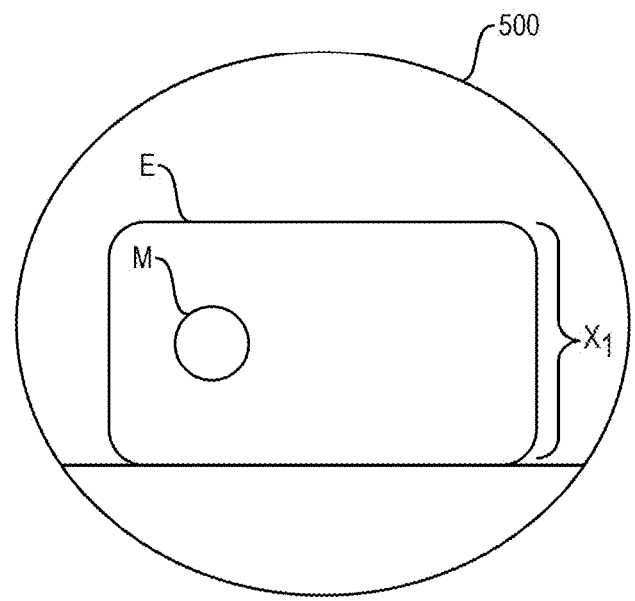
FIGS. 5A and 5B are cross sectional images that may be acquired by a medical imaging system.
Figure 5B:
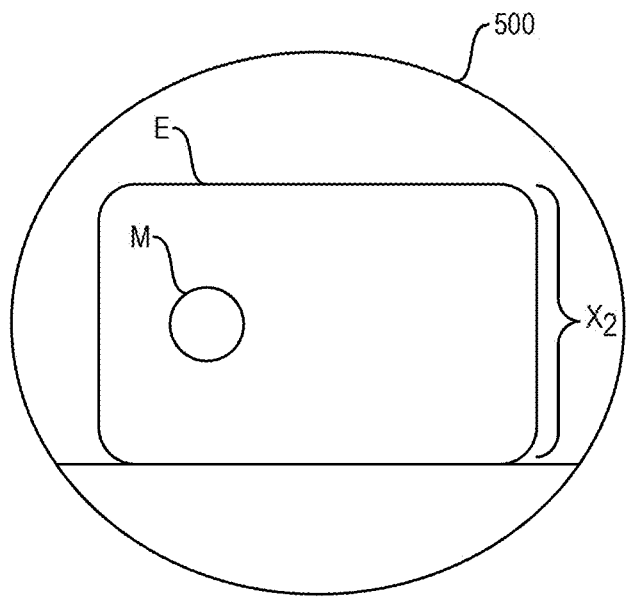

FIG. 5A is a cross-sectional image 500A of an examinee E that may be acquired by a medical imaging system. FIG. 5B shows a cross-sectional image 500B of the examinee E affected by respiratory motion (e.g., an expansion of the body cavity during inhalation). As a scanner, such as the CT scanner in FIG. 4, takes multiple image slices, the deformation may create deformations and/or other dynamic changes in the volumetric scan. In the cross-sectional image 500A of FIG. 5A, the height of the cross section of examinee E's body is X1. In the cross-sectional image 500B of FIG. 5B, because of inhalation, the height of the cross section of examinee E's body is slightly higher to X2. Because the CT scanner is taking multiple slices along the examinee E along direction L, sudden movement between slices (e.g., the cross-sectional image 500A and/or 500B) creates a significant variance that results in a distorted volumetric image within the cartesian plane. In each cross-sectional image 500A and 500B, a mass M may be located within the scan, and its relative position within the volumetric scan may be detected.

Referring back to FIG. 4, the examinee E may be wearing a garment 450 consistent with principles of the present invention. The garment 450 may be in communication with a light emitter 460 that transmits light through FBGs (not shown in FIG. 4) embedded within the garment 450. As the examinee E passes through the CT scanner along direction L, a processor 470 including an FBG data acquisition module 472 receives data from the light sensors (not shown in FIG. 4) attached to the FBGs. A comparator 475 in the processor 470 can identify the effective shifts in the refractive index of the FBGs, due to axial strain on the FBGs and suggest deformations and/or changes in the surface of the object within the garment. As those deformations and/or changes are detected, the processor 470 may send deformation correction information to the image reconstruction device 420 to allow for image compensation for any movement. In other embodiments, the processor 470, including the FBG data acquisition module 472 and comparator 475, may be included in the same apparatus as the data collection device 418 and the image reconstruction device 420.

Figure 6:
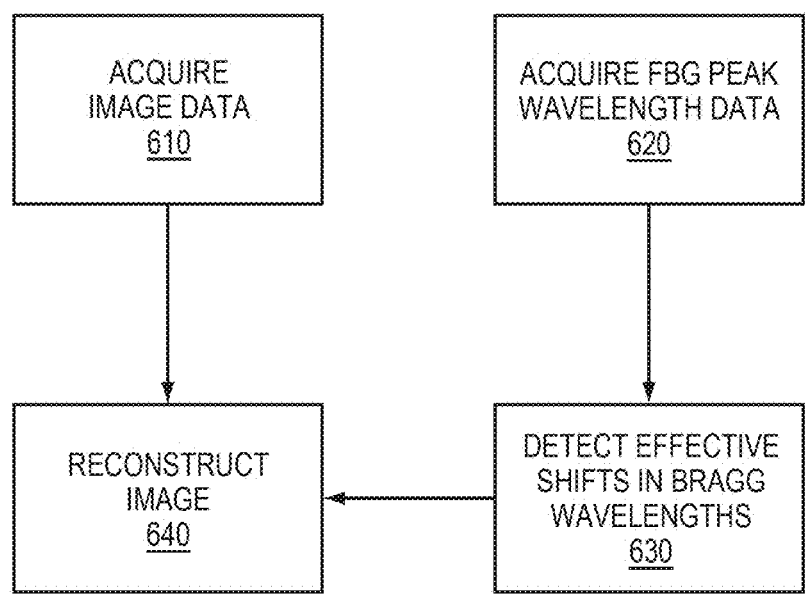
FIG. 6 is a flowchart illustrating a method of compensating for body deformation during image acquisition.

FIG. 6 is a flowchart illustrating a method of compensating for body deformation during image acquisition of an examinee. As the image data of the examinee is acquired at step 610, peak wavelength data in acquired at step 620 from a plurality of fiber Bragg gratings (FBGs) disposed on the body of the examinee. Effective shifts of the Bragg wavelengths of the FBGs caused by body deformation during image acquisition are detected at step 630. If shifts are detected, the acquired image data is corrected at step 640 during image reconstruction in order to compensate for body deformation and/or other dynamic changes during the image scan based on the effective shifts of the Bragg wavelengths of the FBGs aligned along the cartesian coordinate system.

In other embodiments consistent with principles of the present invention, a wearable clothing like device with embedded FBGs for real time detection of respiratory motion may be used to detect body motion (e.g. motion induced by respiration, or muscle spasms) in order to assist with targeted delivery of therapy, such as external beam radiotherapy. By detecting body motion, the therapy may adjust positioning and deliver the maximum dose to a tumor or other disease tissue and the minimum dose to the surrounding healthy tissue.

Figure 7:
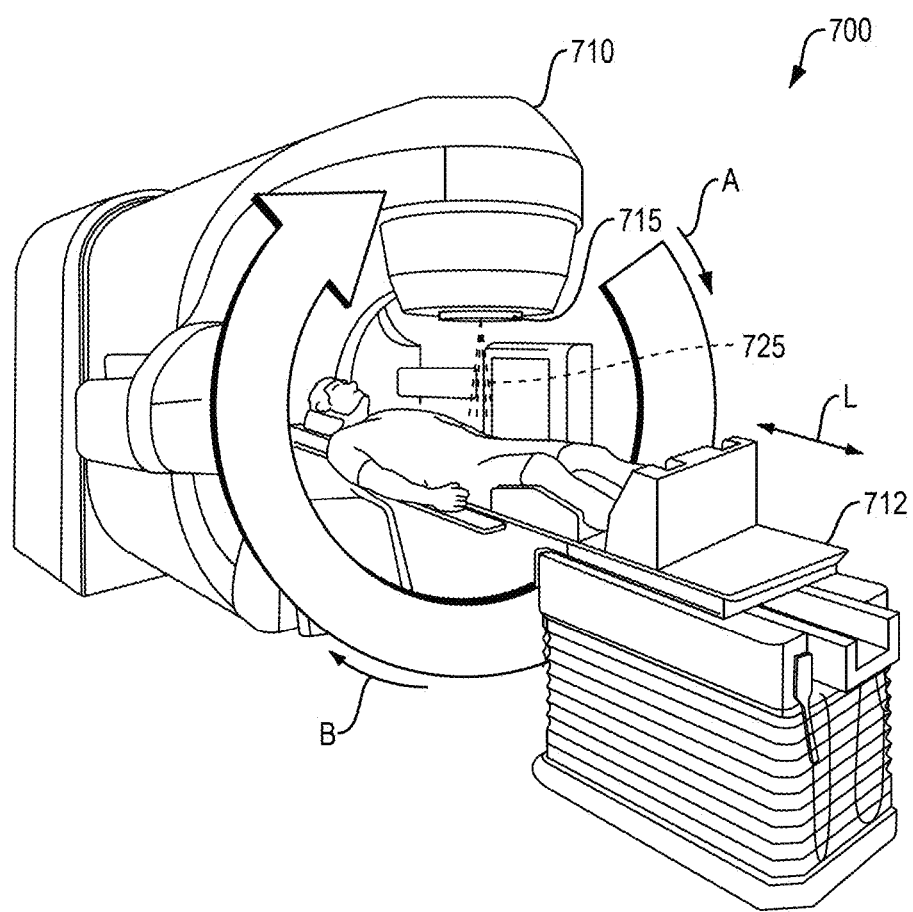
FIG. 7 is an exemplary medical device for external beam treatment in which embodiments consistent with the present invention may be used.

FIG. 7 is an exemplary medical device 700 for external beam treatment in which embodiments consistent with the present invention may be used. A medical linear accelerator (LINAC) is a commonly used device for external beam radiation treatments for patients with cancer. A linear accelerator includes a gantry 710 that typically uses high Radio-Frequency (RF) electromagnet waves to accelerate charged particles (i.e., electrons) to high energies in a linear path, inside a tube like structure called the accelerator waveguide (not shown in FIG. 7). In alternate embodiments, the medical device may include multiple emitters. An emitter 715 emits high energy X-rays 725 from the machine, directed to the patient's tumor. The patient lies on a moveable treatment table 712. The patient is positioned, and such position may be monitored using lasers or mechanical means (not shown in FIG. 7). The treatment table moves in and out of the gantry in direction L. In some alternative medical devices, the table may also move the patient from left to right (perpendicular to direction L) and/or up and down (closer or further from the emitter 715). The gantry may be rotated around the patient, and radiation treatment may be delivered to a tumor or other disease tissue within a patient from many angles by rotating the gantry and moving the treatment couch.

Figure 8:
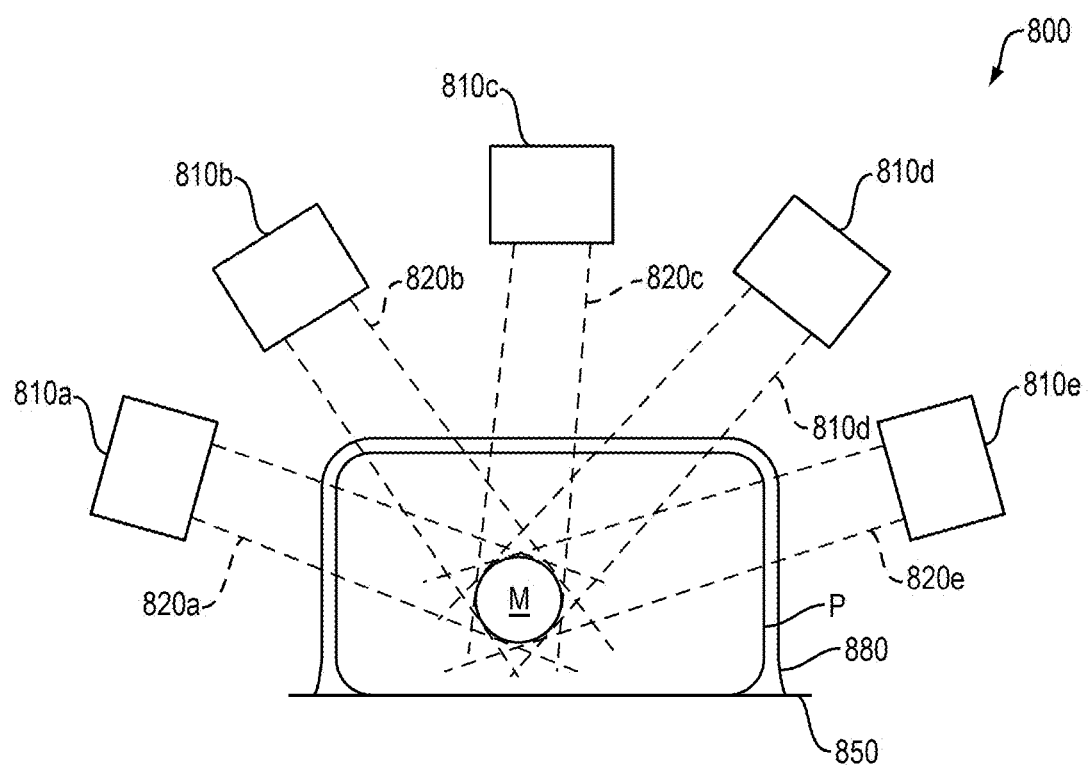
FIG. 8 is a cross sectional view of a body illustrating external beam treatment by the medical device FIG. 7.

FIG. 8 is a cross sectional view 800 of a patient P illustrating external beam treatment by the medical device FIG. 7. The illustration shows an emitter at various positions 810*a-e* as it rotates around the patient P. At the first position 810*a*, the emitter directs some form of beam treatment, such as radiation therapy, through the patient at the mass M. As the gantry rotates through a second position 810*b*, the beam continues to pass through the patient from a different angle, but continues to target the mass M. The radiation treatment passes through healthy tissue, but because the emitter continues to rotate, the exposure to the radiation in the healthy tissue is minimized. Consistent with principles of the invention, a device that includes FBGs may be disposed on the patient P. For example, the patient P may wear a garment 880 that includes FBGs (not shown in FIG. 8) embedded within the garment. As discussed above with respect to FIG. 2A, FIG. 2B, and FIG. 3, the garment 880 may be in communication with a light emitter (not shown in FIG. 8) that transmits light through the FBGs embedded within the garment 880. As the patient P passes through the medical device and receives treatment, a processor similar to the described in connection with FIG. 4, including a data acquisition module receives data from the light sensors attached to the FBGs. Effective shifts in the refractive index of the FBGs, due to axial strain on the FBGs suggest deformations and/or dynamic changes in the surface of the object within the garment, allowing the medical device to shift the positioning of the patient or the emitters in order to better target the mass M and minimize dosage to non-targeted tissues.

By using simultaneously acquired anatomic or functional imaging data along with motion and deformation data on patients wearing a garment embedded with one or more FBGs, one can estimate the motion of internal organs and tumors by employing machine learning algorithms, such as a regression or decision tree algorithm. The image data may be correlated with the motion and deformation data such that the better track objects, such as internal organs, tumors, or other disease tissue within the scanned images. As more image data is obtained, displacement estimations based on detected motion may be further refined. These machine learning techniques can be used during imaging and therapy procedures conducted with the embedded FBG patient motion/body deformation sensing devices (e.g., wearables, garments, etc.) for improving diagnostic image quality and radiation therapy treatment efficacy.

Figure 9:
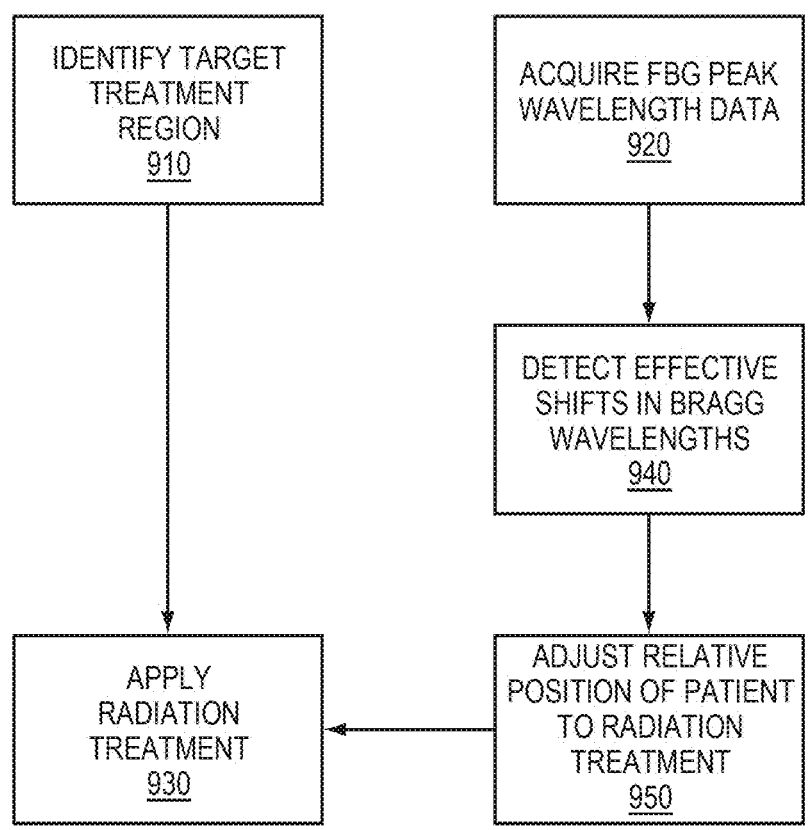
FIG. 9 is a flowchart illustrating a method of compensating for body deformation during external beam treatment.

FIG. 9 is a flowchart illustrating a method of compensating for dynamic changes in the body (e.g., body deformation, respiratory motion, and/or the like) during external beam treatment. As the medical device identifies a target region of a body for external beam treatment in step 910, peak wavelength data is acquired at step 920 from a plurality of fiber Bragg gratings (FBGs) disposed on the body of the examinee. External beam treatment is directed to the target region in step 930. Effective shifts of the Bragg wavelengths of the FBGs caused by body deformation and/or changes during treatment are detected at step 940. In step 950, upon detecting any shifts, the external beam treatment may be shifted to compensate for body deformation and/or changes during an image scan based on the effective shifts of the Bragg wavelengths of the FBGs aligned along the cartesian coordinate system to maintain focus on the target region. In some embodiments, re-directing the external beam treatment may include not applying the treatment to the body by withholding the application of radiation. The relative position of the patient to the radiation treatment may be adjusted by either moving the position of the emitter in the gantry or the treatment table.

The low attenuation properties of a device (e.g., a garment) with embedded FBGs allows it to provide more accurate medical imaging and radiotherapy with little to no interference. In addition, it may also increase patient comfort and reduce radiation dose. Such a device will also open the possibility to make a new class of low-cost scanners as the imaging is done as a function of body deformation and/or changes and can make such imaging modalities more widely accessible even to the most cost sensitive population groups.

While example embodiments have been particularly shown and described, it will be understood by those skilled in the art that various changes in form and details may be made therein without departing from the scope encompassed by the appended claims.

It should be understood that the example embodiments described above may be implemented in many different ways. In some instances, the various methods and machines described herein may each be implemented by a physical, virtual or hybrid general purpose computer having a central processor, memory, disk or other mass storage, communication interface(s), input/output (I/O) device(s), and other peripherals. The general-purpose computer is transformed into the machines that execute the methods described above, for example, by loading software instructions into a data processor, and then causing execution of the instructions to carry out the functions described, herein.

As is known in the art, such a computer may contain a system bus, where a bus is a set of hardware lines used for data transfer among the components of a computer or processing system. The bus or busses are essentially shared conduit(s) that connect different elements of the computer system, e.g., processor, disk storage, memory, input/output ports, network ports, etcetera, which enables the transfer of information between the elements. One or more central processor units are attached to the system bus and provide for the execution of computer instructions. Also attached to system bus are typical I/O device interfaces for connecting various input and output devices, e.g., keyboard, mouse, displays, printers, speakers, etcetera, to the computer. Network interface(s) allow the computer to connect to various other devices attached to a network. Memory provides volatile storage for computer software instructions and data used to implement an embodiment. Disk or other mass storage provides non-volatile storage for computer software instructions and data used to implement, for example, the various procedures described herein.

Embodiments may therefore typically be implemented in hardware, firmware, software, or any combination thereof.

In certain embodiments, the procedures, devices, and processes described herein constitute a computer program product, including a non-transitory computer-readable medium, e.g., a removable storage medium such as one or more DVD-ROMs, CD-ROMs, diskettes, tapes, etcetera, that provides at least a portion of the software instructions for the system. Such a computer program product can be installed by any suitable software installation procedure, as is well known in the art. In another embodiment, at least a portion of the software instructions may also be downloaded over a cable, communication and/or wireless connection.

Further, firmware, software, routines, or instructions may be described herein as performing certain actions and/or functions of the data processors. However, it should be appreciated that such descriptions contained herein are merely for convenience and that such actions in fact result from computing devices, processors, controllers, or other devices executing the firmware, software, routines, instructions, etcetera.

It also should be understood that the flow diagrams, block diagrams, and network diagrams may include more or fewer elements, be arranged differently, or be represented differently. But it further should be understood that certain implementations may dictate the block and network diagrams and the number of block and network diagrams illustrating the execution of the embodiments be implemented in a particular way.

Accordingly, further embodiments may also be implemented in a variety of computer architectures, physical, virtual, cloud computers, and/or some combination thereof, and, thus, the data processors described herein are intended for purposes of illustration only and not as a limitation of the embodiments.

While this invention has been particularly shown and described with references to example embodiments thereof, it will be understood by those skilled in the art that various changes in form and details may be made therein without departing from the scope of the invention encompassed by the appended claims.

What is claimed is:

1. A method of compensating for dynamic changes in a body of a patient during a controlled interaction with the body, the method comprising:
   acquiring data from a sensing device disposed on the body;
   detecting a change along at least one optical fiber of the sensing device caused by dynamic changes associated with the body during the controlled interaction;
   generating a respiratory gating signal based on the change along the at least one optical fiber of the sensing device measured over time; and
   controlling relative movement between the body and an interactive device in response to the respiratory gating signal to compensate for the dynamic changes associated with the body during the controlled interaction.

2. The method of claim 1, wherein the sensing device comprises at least one fiber Bragg grating (FBG).

3. The method of claim 2, wherein:
   the acquiring data from the sensing device comprises acquiring wavelength data from the at least one FBG;
   the detecting the change along the at least one optical fiber comprises detecting effective shifts of Bragg wavelengths in the wavelength data; and
   the generating the respiratory gating signal comprises generating the respiratory gating signal based on the effective shifts of the Bragg wavelengths.

4. The method of claim 1, wherein the dynamic changes associated with the body include at least one of body deformation, respiratory motion, tumor motion, or organ motion.

5. The method of claim 1, further comprising:
   pausing the controlled interaction when the respiratory gating signal indicates at least one of a release of a voluntary breath hold, a voluntary excursion associated with the voluntary breath hold, or an involuntary excursion associated with the voluntary breath hold.

6. The method of claim 1, wherein the respiratory gating signal is associated with at least one of a Respiratory Deep Inspiration Breath Hold or an Expiration Breath Hold.

7. The method of claim 1, wherein the controlled interaction is at least one of an image acquisition, an external beam treatment, a focused energy treatment procedure, a biopsy procedure, or a guided placement of an interventional device.

8. The method of claim 7, wherein the external beam treatment is external beam radiotherapy or proton beam therapy.

9. A method of compensating for dynamic changes in a body of a patient during a controlled interaction with the body, the method comprising:
   acquiring wavelength data from at least one fiber Bragg grating (FBG) disposed on a body;
   detecting effective shifts of Bragg wavelengths in the wavelength data caused by dynamic changes associated with the body during the controlled interaction;
   generating a respiratory gating signal based on the effective shifts of the Bragg wavelengths measured over time; and
   controlling an interactive device, based on the respiratory gating signal, to pause the controlled interaction during the dynamic changes associated with the body.

10. The method of claim 9, wherein the dynamic changes associated with the body include at least one of body deformation, respiratory motion, tumor motion, or organ motion.

11. The method of claim 9, wherein the respiratory gating signal is associated with a voluntary breath hold, the controlling the interactive device comprises controlling the interactive device when the respiratory gating signal indicates at least one of a release of the voluntary breath hold, a voluntary excursion associated with the voluntary breath hold, or an involuntary excursion associated with the voluntary breath hold.

12. The method of claim 9, wherein the respiratory gating signal is associated with at least one of a Respiratory Deep Inspiration Breath Hold or an Expiration Breath Hold.

13. The method of claim 9, wherein the controlled interaction is at least one of image acquisition or a therapeutic interaction.

14. The method of claim 9, wherein the controlled interaction is a therapeutic interaction, the therapeutic interaction including at least one of an external beam treatment, a focused energy treatment procedure, a biopsy procedure, or a guided placement of an interventional device.

15. The method of claim 14, wherein the external beam treatment is external beam radiotherapy or proton beam therapy.

16. A method of compensating for dynamic changes in a body of a patient during a controlled interaction with the body, the method comprising:
- acquiring wavelength data from at least one fiber Bragg grating (FBG) disposed on a body;
- detecting effective shifts of Bragg wavelengths in the wavelength data caused by dynamic changes associated with the body during the controlled interaction;
- generating a respiratory gating signal based on the effective shifts of the Bragg wavelengths measured over time; and
- controlling a scanning device based on the respiratory gating signal such that image data is not acquired during the dynamic changes associated with the body.

17. The method of claim 16, wherein the dynamic changes associated with the body include at least one of body deformation, respiratory motion, tumor motion, or organ motion.

18. The method of claim 16, wherein the respiratory gating signal indicates a voluntary breath hold.

19. The method of claim 18, further comprising:
- pausing the controlled interaction when the respiratory gating signal indicates at least one of a release of the voluntary breath hold, a voluntary excursion associated with the voluntary breath hold, or an involuntary excursion associated with the voluntary breath hold.

20. The method of claim 16, further comprising:
- controlling an interactive device based at least in part on the acquired image data to perform the controlled interaction with the body while compensating for the dynamic changes.

21. The method of claim 16, wherein the respiratory gating signal is associated with at least one of a Respiratory Deep Inspiration Breath Hold or an Expiration Breath Hold.

22. The method of claim 16, wherein the controlled interaction is a therapeutic interaction, the therapeutic interaction including at least one of an external beam treatment, a focused energy treatment procedure, a biopsy procedure, or a guided placement of an interventional device.

23. The method of claim 22, wherein the external beam treatment is external beam radiotherapy or proton beam therapy.

24. A method of compensating for dynamic changes in a body of a patient during a controlled interaction with the body, the method comprising:
- acquiring wavelength data from at least one fiber Bragg gratings (FBG) disposed on a body;
- detecting effective shifts of Bragg wavelengths in the wavelength data caused by dynamic changes associated with the body during the controlled interaction;
- generating a respiratory gating signal based on the effective shifts of the Bragg wavelengths measured over time;
- controlling a scanning device, based at least in part on the respiratory gating signal, to acquire image data of a target region of the body while compensating for the dynamic changes associated with the body; and
- controlling an interactive device, based at least in part on the respiratory gating signal and the acquired image data, to perform the controlled interaction with the target region.

25. The method of claim 24, wherein the dynamic changes associated with the body include at least one of body deformation, respiratory motion, tumor motion, or organ motion.

26. The method of claim 24, wherein the respiratory gating signal indicates a voluntary breath hold.

27. The method of claim 26, further comprising:
- pausing the controlled interaction when the respiratory gating signal indicates at least one of a release of the voluntary breath hold, a voluntary excursion associated with the voluntary breath hold, or an involuntary excursion associated with the voluntary breath hold.

28. The method of claim 24, wherein the respiratory gating signal is associated with at least one of a Respiratory Deep Inspiration Breath Hold or an Expiration Breath Hold.

29. The method of claim 24, wherein the controlled interaction is a therapeutic interaction, the therapeutic interaction including at least one of an external beam treatment, a focused energy treatment procedure, a biopsy procedure, or a guided placement of an interventional device.

30. The method of claim 29, wherein the external beam treatment is external beam radiotherapy or proton beam therapy.

* * * * *